(12) United States Patent
Joshi et al.

(10) Patent No.: US 6,355,676 B1
(45) Date of Patent: Mar. 12, 2002

(54) FUMARIC ACID MICRO TABLETS

(75) Inventors: Rajendra Kumar Joshi, Zürich; Hans-Peter Strebel, Muri, both of (CH)

(73) Assignee: Fumapharm AG, Muri (CH)

( * ) Notice: Subject to any disclaimer, the term of this patent is extended or adjusted under 35 U.S.C. 154(b) by 0 days.

(21) Appl. No.: 09/743,978

(22) PCT Filed: Oct. 8, 1999

(86) PCT No.: PCT/EP99/07568

§ 371 Date: Jan. 17, 2001

§ 102(e) Date: Jan. 17, 2001

(87) PCT Pub. No.: WO00/10681

PCT Pub. Date: Mar. 2, 2000

(30) Foreign Application Priority Data

Oct. 20, 1998 (DE) .......................... 198 48 260

(51) Int. Cl.⁷ ............................. A61K 31/315
(52) U.S. Cl. ...................... 514/494; 514/547
(58) Field of Search .................. 514/547, 494

(56) References Cited

U.S. PATENT DOCUMENTS

| | | | |
|---|---|---|---|
| 4,851,439 A | 7/1989 | Speiser et al. | 514/547 |
| 4,959,389 A | 9/1990 | Speiser et al. | 514/494 |
| 5,424,332 A * | 6/1995 | Speiser et al. | 514/547 |
| 5,451,667 A * | 9/1995 | Speiser et al. | 536/41 |

FOREIGN PATENT DOCUMENTS

| | | |
|---|---|---|
| DE | 2530372 | 1/1977 |
| DE | 2621214 | 11/1977 |
| DE | 3834794 | 4/1990 |
| EP | 0312697 | 4/1989 |

OTHER PUBLICATIONS

Sebök, Bela et al., "Antiproliferative and Cytotoxic profiles of Antipsoriatic Fumaric Acid Derivatives in Keratinocyte Cultures", European Journal of Pharm., Environ., Toxicol. Pharmacol. Sect., 1994, vol. 270, pp. 79–87.

Nibbering, P.H. et al., "Intracellular Signalling by Binding Sites for the Antipsoratic Agent Monomethylfumarate on Human Granulocytes", British J. Dermatiol., 1997, vol. 137, pp. 65–75.

Altmeyer, P. et al., "Systemische Therapie der Psoriasis", T & E Dermatologie Jg., 1997, vol. 27, pp. 380–382, 384—not translated.

Nibbering, Peter H., "Effects of Monomethylfumarate on Human Granulocytes", Journal of Investigative Dermatology, 1993, vol. 101, pp. 37–42.

Medline Abstract of Bayard et al., "Peroral long–term treatment of psoriasis using fumaric acid derivatives", Hautarzt, 1987 May, 38(5), pp. 279–285.

* cited by examiner

Primary Examiner—James H. Reamer
(74) Attorney, Agent, or Firm—Sieberth & Patty, L.L.C.

(57) ABSTRACT

The present invention relates to the use of one or more salts of fumaric acid monoalkyl esters of the general formula

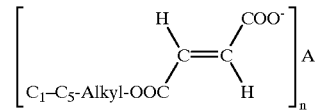

optionally in admixture with dialkyl fumarate of the formula

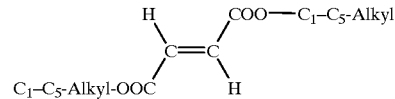

wherein A is a bivalent cation from the series consisting of Ca, Mg, Zn or Fe or a monovalent cation from the series Li, Na or K, respectively, and n denotes the numeral 1 or 2 depending on the type of cation, and, optionally, commonly used pharmaceutical excipients and vehicles for preparing a pharmaceutical composition in the form of micro-tablets or micro-pellets for the treatment of psoriatic arthritis, neurodermatitis, psoriasis and enteritis regionalis Crohn.

54 Claims, No Drawings

FUMARIC ACID MICRO TABLETS

This application is a 371 continuation of PCT Application PCT/EP99/07568, filed Oct. 8, 1999, the text of which is not in English, which PCT Application claims priority on German Application No. 198 48 260.4, filed Oct. 20, 1998, the text of which is not in English.

The present invention relates to the use of certain fumaric acid monoalkyl ester salts either alone or in combination with a dialkyl fumarate for preparing micro-tablets for the treatment of psoriatic arthritis, neurodermatitis, psoriasis and enteritis regionalis Crohn.

EP-A-0 188 749 already describes fumaric acid derivatives and pharmaceutical compositions containing the same for the treatment of psoriasis. Likewise, pharmaceutical compositions for treating psoriasis which contain a mixture of fumaric acid and other fumaric acid derivatives are known from DE-A-25 30 372. A content of free fumaric acid is obligatory.

DE-A-26 21 214 describes drugs for treating psoriasis which contain fumaric acid monoethyl ester and mineral salts thereof as the active ingredient. The use of fumaric acid monoethyl ester salts of calcium, zinc and magnesium and of fumaric acid dimethyl ester for the treatment of psoriasis is also known from the publication "Hautarzt" (Dermatologist) 1987, pages 279 to 285.

Finally, EP-A-0 312 697 discloses pharmaceutical compositions containing one or more compounds selected from the calcium, magnesium, zinc and iron salts of fumaric acid monomethyl ester, alone or preferably in admixture with $C_{1-5}$ alkyl fumarates. A preparation according to example 4 of this document contains 87.5 mg of monoethyl fumarate Ca salts, 120.0 mg of dimethyl fumarate, 5.0 mg of monoethyl fumarate Mg salt and 3.0 mg of monoethyl fumarate Zn salt, which corresponds to 164 mg of fumaric acid. The preparation is presented in the form of enteric-coated tablets and is approved for distribution in the German market under the trademark Fumaderm®.

As early as phase 3 of the clinical tests and in post-marketing studies of this product, it was found that about 60% of the patients developed gastro-intestinal symptoms in the form of diarrhoea, stomach pains and bloating during the initial phase of the Fumaderm® therapy. Other side effects are so-called flushes, i.e. redness of the face, and sensations of heat.

Even though the tablets are generally tolerated relatively well, the above-mentioned symptoms keep occurring, especially at the onset of therapy. In the course of the treatment, these undesirable side effects often decrease. However, the intake of Fumaderm® causes severe gastro-intestinal complaints in some patients. These symptoms in the stomach and intestine affect patient compliance and can be so unpleasant for the patient that therapy is sometimes discontinued.

Therefore, it was the object of the present invention to provide a pharmaceutical preparation which avoids the above-mentioned side effects, especially gastro-intestinal complaints, while the same pharmaceutical ingredients are administered.

Tests carried out by the Applicant have shown that methyl hydrogen fumarate, a metabolite of dimethyl fumarate which forms the main component of the preparation Fumaderm® initially increases the endotoxin-stimulating TNF-α secretion in human mononuclear cells of the peripheral blood (peripheral blood mononuclear cells =PBMC) and in isolated monocytes. With multiple re-exposure, the endotoxin-induced increase in TNF-α secretion is reduced, i.e. adaptation takes place.

Possibly, this initial induction of TNF-α is responsible for the known side effect of the Fumaderm® preparation such as gastro-intestinal complaints or the flush symptoms. The tendency towards decrease of endotoxin-induced TNF-α secretion after repeated methyl hydrogen fumarate exposure may be an explanation for the adaptation effect, i.e. the decrease of side effects after sustained Fumaderm® therapy. Accordingly, it was the first objective of additional tests to inhibit TNF-α secretion with other drugs and thus to control the side effects of Fumaderm® administration.

Surprisingly and unexpectedly, it was found in the course of these tests that formulation of the active ingredient in the form of micro-tablets resulted in a substantial reduction of gastro-intestinal symptoms. Therefore, the object of the invention is achieved by using one or more fumaric acid monoalkyl ester salts of the general formula

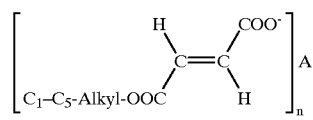

optionally in admixture with dialkyl fumarate of the formula

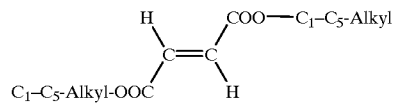

wherein A is a bivalent cation from the series consisting of Ca, Mg, Zn or Fe or a monovalent cation from the series Li, Na or K, respectively, and n denotes the numeral 1 or 2 depending on the type of cation, and, optionally, commonly used pharmaceutical excipients and vehicles for preparing a pharmaceutical composition in the form of micro-tablets or micro-pellets for the treatment of psoriatic arthritis, neurodermatitis, psoriasis and enteritis regionalis Crohn.

Preferably, the size or the mean diameter, respectively, of the micro-pellets or micro-tablets is in the range of 300 to 2.000 μm, especially in the range of 500 to 1.500 μm and most preferably 1.000 μm.

The micro-tablets or micro-pellets may be filled in capsules or sachets and administered in this form. In addition, the micro-tablets themselves or the capsules may be provided with an enteric coating which is applied by conventional processes. Capsules may be hard or soft gelatine capsules.

Preferred compositions according to the invention contain the calcium salt of the fumaric acid monomethyl ester and/or the calcium salt of the fumaric acid monoethyl ester, optionally in admixture with dimethyl fumarate. The total weight of the active ingredients is 10 to 300 mg. Preferably, the composition in the form of micro-tablets contains 10 to 290 parts by weight of the fumaric acid monoalkyl ester (calcium salt) and 290 to 10 parts by weight of dimethyl fumarate. According to another embodiment, this composition may also contain 1 to 50 parts by weight of fumaric acid monoalkyl ester zinc salt.

Another preferred embodiment in the form of micro-tablets contains 1 to 250 parts by weight of fumaric acid monoalkyl ester (calcium salt), 250 to 10 parts by weight of dimethyl fumarate, 1 to 50 parts by weight of fumaric acid monoalkyl ester (magnesium salt) and 1 to 50 parts by weight of fumaric acid monoalkyl ester (zinc salt), the total weight of the active ingredients being 30 to 300 mg.

For systemic initiation as well as for termination of the treatment in stages (decreasing dosage), a low dose is advantageous. Such a dose may, for example, consist of 30 mg of dimethyl fumarate, 20 mg of monoethyl fumarate (calcium salt) and 3 mg of monoethyl fumarate or monomethyl fumarate (zinc salts). Therapeutic doses after an initial phase may, for example, be comprised of 20 mg of dimethyl fumarate, 87 mg of monoethyl fumarate (calcium salt) and 3.0 mg of monoethyl fumarate or monomethyl fumarate (zinc salt).

For example, the fumaric acid derivatives used in the invention are obtained according to the processes described in EP 0 312 697.

Without wishing to be bound by theoretic contemplations, it is assumed that the gastro-intestinal symptoms may be caused by local stimulation of the epithelial cells of the intestine which induces TNF-α secretion. Upon administration of conventional tablets, the ingredients of these tablets are released in the intestine in a concentration which is too high, causing local irritation of the intestinal mucous membrane. As a result of this local irritation very high concentrations of TNF-α are presumably released for a short period of time which may be responsible for the gastrointestinal side effects. On the other hand, when enteric-coated micro-tablets in capsules are applied, locally low concentrations of the active ingredients on the epithelial cells of the intestine are achieved. By peristaltic movements of the stomach, the micro-tablets are gradually moved into the small intestine with enhanced distribution of the active ingredients.

In other words, enteric-coated micro-tablets in the same dose disperse in the stomach already and are fed to the intestine in portions (boluswise), where the active ingredients are released in smaller doses. As a result, local irritation of the epithelial cells of the intestine and the release of TNF-α are avoided. This is a possible explanation for the enhanced toleration of micro-tablets in the gastro-intestinal tract vis-à-vis conventional tablets. However, it was not to be expected that a mere change in galenics would lead to such a drastic reduction of side effects.

The following examples will show the production and action of the micro-tablets according to the invention.

EXAMPLE 1

Preparation of Enteric-coated Micro-tablets in Capsules Containing 87.0 mg of Monoethyl Fumarate-Ca Salt, 120.0 mg of Dimethyl Fumarate and 5.0 mg of Monoethyl Fumarate-Mg Salt, Which Corresponds to a Total of 164 mg of Fumaric Acid Taking the necessary precautions (breathing mask, gloves, protective clothing, etc.), 8.700 kg of monoethyl fumarate-Ca salt, 12.000 kg of dimethyl fumarate, 0.500 kg of monoethyl fumarate-Mg salt and 0.30 kg of monoethyl fumarate-Zn salt are crushed, intensely mixed and homogenised by means of a sieve 800. Then an excipient mixture of the following composition is prepared: 18.00 kg of starch derivative (STA-RX® 1500), 0.30 kg of micro-crystalline cellulose (Avicel® PH 101), 0.75 kg of PVP (Koilidon® 120), 4.00 kg of Primogel®, 0.25 kg of colloidal silicic acid (Aerosil®). The entire powder mixture is added to an active ingredient mixture, homogenised by means of a sieve 200, processed in the usual manner with a 2% aqueous solution of polyvinyl pyrrolidone (Kollidon® K25) to obtain a binder granulate and mixed in a dry state with the outer phase consisting of 0.50 kg of Mg stearate and 1.50 kg of talcum. Then the powder mixture is pressed by the conventional method into convex micro-tablets with a gross mass of 10.0 mg and a diameter of 2.0 mm. Instead of this classic tabletting method other methods for making tablets such as direct tabletting or a method for making solid dispersions by the melt method and the spray drying method may also be used.

The gastric acid-resistant coating may be poured or sprayed on in a classic coating pan or applied in a fluidised-bed apparatus. In order to achieve resistance to gastric acid, portions of a solution of 2.250 kg of hydroxy propyl methyl cellulose phthalate (HPMCP, Pharmacoat® HP 50) are dissolved in a mixture of the following solvents: acetone 13.00 1, ethanol (94% by weight denatured with 2% ketone) 13.50 1 and demineralised water 1.50 1. 0.240 kg of castor oil are added as softening agent to the finished solution and applied in portions to the tablet cores in the usual manner.

After drying is completed, a suspension of the following composition is applied as a film-coat in the same apparatus: talcum 0.340 kg, titanium(VI) oxide Cronus RN 56 0.400 kg, coloured lacquer L red lacquer 86837 0.324 kg, Eudragit E 12.5% 4.800 kg and polyethylene glycol 6000 pH 11 XI 0.120 kg in a solvent mixture of the following composition: 2-propanol 8.170 kg, *aqua demineralisata* 0.200 kg and glycerine triacetate (Triacetin) 0.600 kg.

The enteric-coated micro-tablets are then filled into hard gelatine capsules at a net weight of 500.0 mg and sealed.

EXAMPLE 2

Preparation of enteric-coated Micro-tablets in Capsules Containing 87.0 mg of Monoethyl Fumarate-Ca Salt, 120.0 mg of Dimethyl Fumarate and 5.0 mg of Monoethyl Fumarate-Mg Salt, which Corresponds to a Total of 164 mg of Fumaric Acid Taking the necessary precautions (breathing mask, gloves, protective clothing, etc.), 8.700 kg of monoethyl fumarate-Ca salt, 12.000 kg of dimethyl fumarate, 0.500 kg of monoethyl fumarate-Mg salt and 0.30 kg of monoethyl fumarate-Zn salt are crushed, intensely mixed. and homogenised by means of a sieve 800. Then an excipient mixture of the following composition is prepared: 24.70 kg of micro-crystalline cellulose (Avicel® PH 200), 3.00 kg of croscarmellose sodium (AC-Di-SOL-SD-711), 2.50 kg of talcum, 0.10 kg of anhydrous silica (Aerosil® 200) and 1.00 kg of magnesium stearate. The entire excipient mixture is added to the active ingredient mixture and homogenised. Then the powder mixture is pressed by direct tabletting into convex micro-tablets with a gross mass of 10.0 mg and a diameter of 2.0 mm. Instead of this classic tabletting method other methods for making tablets such as solid dispersions by the melt method, the spray drying method or tabletting of binder granulates may also be used.

The gastric acid-resistant coating may be poured or sprayed on in a classic coating pan or applied in a fluidised-bed apparatus. For example, a solution of 0,94 kg of Eudragita L in isopropanol is prepared which also contains 0.07 kg of dibutyl phthalate. This solution is sprayed onto the tablet cores.

After that, a dispersion of 17.32 kg of Eudragit® L D-55 and a mixture of 2.80 kg of micro-talcum, 2.00 kg of Macrogol 6000 and 0.07 kg of Dimetican in water is prepared and sprayed onto the cores.

The enteric-coared micro-tablets are then filled into hard gelatine capsules at a net weight of 760.0 mg and sealed.

Therapy examples

Micro-tablets containing the same four active ingredients in the same quantitative composition as the commercial product Eumaderm® were prepared according to the above production examples. A Fumaderm® tablet with enteric coating corresponds to about 102 enteric-coated micro-tablets having the same composition. As described in the production examples, these micro-tablets are filled into capsules for more convenient administration. Two capsules correspond to one tablet of Fumadermo.

For easier comparison, two patients who developed severe gastro-intestinal symptoms during therapy with Fumaderm® tablets were treated with the enteric-coated micro-tablets according to the invention. After administration of these micro-tablets, these patients surprisingly no longer complained about gastro-intestinal troubles which had been observed during administration of conventional tablets. The same improvement of psoriasis was observed as with Fumaderm® tablets of the prior art. Under certain circumstances, a smaller dose may suffice to achieve clinical success when micro-tablets are administered.

The results of the treatment are presented in the following table:

|  | Patient 1 | Patient 2 | Product* |
|---|---|---|---|
| Initials | M.M. | W.F. |  |
| Age | 63 | 54 |  |
| Sex | female | male |  |
| Dose | Jan. 1 to April 1, 1998 of Fumaderm initial | 1985: 3 tablets of Fumaderm/day | Fumaderm ® initial/ Fumaderm ® |
| GI symptoms | cramps, pain | pain in the epigastric region | Fumaderm ® initial/ Fumaderm ® |
| Severity of GI symptoms | severe | severe | Fumaderm ® initial/ Fumaderm ® |
| Clinical evaluation of psoriasis | satisfactory | satisfactory | Fumaderm ® initial/ Fumaderm ® |
| Interruption of therapy | none | 1985– May 12, 1998 | Fumaderm ® initial/ Fumaderm ® |
| Dose | Apr. 1–6, 1998 3 capsules/day Apr. 7– May 10, 1998 9 capsules/day May 11– Aug. 31, 1998 3 capsules/day | May 13– 20, 1998 3 capsules/day May 21– July 1, 1998 6 capsules/day | Fumaderm ® P mikro |
| GI symptoms | none | May 15– 18, 1998 winds | " |
| Severity of symptoms | — | slight | " |
| Clinical evaluation of psoriasis | very good | good | " |

*1 Fumaderm ® tablet corresponds to two capsules of Fumaderm P mikro
GI = gastrointestinal The table shows that even an increased dose of micro-tablets (9 capsules per day) had no or only slight side effects, while the lower dose of the commercial product Fumaderm® already caused severe gastro-intestinal symptoms.

The results of the treatment also show that the effectiveness of micro-tablets for treating psoriasis is at least equivalent, if not better than that of the commercial product. On the whole, the formulation of fumaric acid derivates in the form of micro-tablets therefore show a significant improvement vis-à-vis therapy with conventional tablets.

What is claimed is:

1. A method of preparing a pharmaceutical composition for treatment of psoriatic arthritis, neurodermatitis, psoriasis, or enteritis regionalis Crohn, which method comprises forming micro-tablets or micro-pellets from one or more salts of fumaric acid monoalkyl esters of the general formula

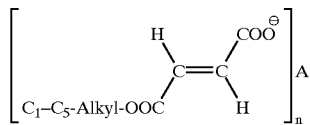

optionally in admixture with dialkyl fumarate of the formula

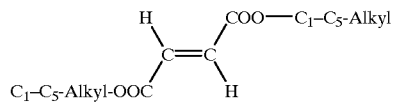

wherein A is a bivalent cation from the series consisting of Ca, Mg, Zn, or Fe, or a monovalent cation from the series Li, Na, or K, respectively, and n denotes the numeral 1 or 2 depending on the type of cation, and, optionally, at least one pharmaceutically acceptable excipient or vehicle.

2. The method according to claim 1, characterized in that the calcium salt of fumaric acid monoethyl ester or monomethyl ester is the salt of fumaric acid monoalkyl ester used in forming said composition.

3. The method according to claim 1, characterized in that the calcium salt of the fumaric acid monoalkyl ester in admixture with dimethyl fumarate is used in forming said composition.

4. The method according to claim 2, characterized in that the calcium salt of fumaric acid monoethyl or monomethyl ester is used in admixture with dimethyl fumarate in forming said composition.

5. The method according to claim 1, characterized in that the calcium and zinc salts of the fumaric acid monoalkyl ester in admixture with dimethylfumarate are used in forming said composition.

6. The method according to claim 1, characterized in that the calcium, magnesium, and zinc salts of the fumaric acid monoethyl ester in admixture with dimethylfumarate are used in forming said composition.

7. The method according to claim 1, characterized in that the salt of the fumaric acid monoalkyl ester used in forming said composition is the calcium salt of the fumaric acid monoalkyl ester, and the amount thereof per dosage form is 10 to 300 mg, the total weight of the active ingredients per dosage form being 10 to 300 mg.

8. The method according to any of claims 2 to 6, characterized in that said calcium salt is used in an amount per dosage form of 10 to 300 mg, the total weight of the active ingredients per dosage form being 10 to 300 mg.

9. The method according to claim 3, characterized in that 10 to 290 parts by weight of the calcium salt of the fumaric acid monoalkyl ester and 290 to 10 parts by weight of dimethyl fumarate are used in forming said composition, the total weight of the active ingredients per dosage form being 20 to 300 mg.

10. The method according to claim 9, characterized in that said calcium salt is the calcium salt of fumaric acid monoethyl or monomethyl ester.

11. The method according to claim 5, characterized in that 10 to 250 parts by weight of the calcium salt of the fumaric acid monoalkyl ester, 1 to 50 parts by weight of dimethyl fumarate, and 1 to 50 parts by weight of the zinc salt of the fumaric acid monoalkyl ester are used in forming said composition, the total weight of the active ingredients per dosage form being 20 to 300 mg.

12. The method according to claim 1, characterized in that 10 to 250 parts by weight of the calcium salt of the fumaric acid monoalkyl ester, 250 to 10 parts by weight of dimethyl fumarate, 1 to 50 parts by weight of the magnesium salt of the fumaric acid monoalkyl ester and 1 to 50 parts by weight of the zinc salt of the fumaric acid monoalkyl ester are used in forming said composition, the total weight of the active ingredients per dosage form being 30 to 300 mg.

13. The method according to claim 12, characterized in that the said calcium salt is the calcium salt of fumaric acid monoethyl ester or the calcium salt of fumaric acid monomethyl ester.

14. The method according to claim 12, characterized in that said calcium salt, said magnesium salt, and said zinc salt are, respectively, the calcium, the magnesium, and the zinc salts of fumaric acid monoethyl ester.

15. The method according to any of claims 1, 2, 3, 4, 5, 6, 7, 9, 10, 11, 12, 13, or 14 wherein the micro-tablets or micro-pellets are provided with an enteric coating (coating resistant to gastric acid).

16. The method according to any of claims 1, 2, 3, 4, 5, 6, 7, 9, 10, 11, 12, 13, or 14 wherein the micro-tablets or micro-pellets are filled into capsules or sachets.

17. The method according to claim 8 wherein the micro-tablets or micro-pellets are provided with an enteric coating (coating resistant to gastric acid).

18. The method according to claim 8 wherein the micro-tablets or micro-pellets are filled into capsules or sachets.

19. A pharmaceutical composition for treatment of psoriatic arthritis, neurodermatitis, psoriasis, or enteritis regionalis Crohn, which composition comprises micro-tablets or micro-pellets comprising at least one salt of a fumaric acid monoalkyl ester of the formula

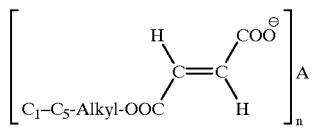

optionally in admixture with dialkyl fumarate of the formula

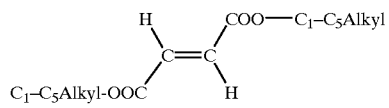

wherein A is a bivalent cation from the series consisting of Ca, Mg, Zn, or Fe, or a monovalent cation from the series Li, Na, or K, respectively, and n denotes the numeral 1 or 2 depending on the type of cation, and, optionally, at least one pharmaceutically acceptable excipient or vehicle.

20. A composition according to claim 19 wherein said at least one salt of a fumaric acid monoalkyl ester is the calcium salt of fumaric acid monoethyl ester or of fumaric acid monomethyl ester.

21. A composition according to claim 19 wherein said at least one salt of a fumaric acid monoalkyl ester is the calcium salt of said fumaric acid monoalkyl ester, and wherein dimethyl fumarate is in admixture with said calcium salt in said composition.

22. A composition according to claim 20 wherein dimethylfumarate is in admixture with the calcium salt of fumaric acid monoethyl ester or fumaric acid monomethyl ester in said composition.

23. A composition according to claim 19 wherein said at least one salt of a fumaric acid monoalkyl ester is a mixture of the calcium and the zinc salts of said fumaric acid monoalkyl ester, and wherein dimethylfumarate is in admixture with said calcium and zinc salts in said composition.

24. A composition according to claim 19 wherein said at least one salt of a fumaric acid monoalkyl ester is a mixture of the calcium, the magnesium, and the zinc salts of fumaric acid monoethyl ester, and wherein dimethylfumarate is in admixture with said calcium, magnesium, and zinc salts in said composition.

25. A composition according to claim 19 wherein said at least one salt of a fumaric acid monoalkyl ester is the calcium salt of said fumaric acid monoalkyl ester, and wherein said composition contains per dosage form 10 to 300 mg of said calcium salt, with the total weight of the active ingredients being 10 to 300 mg per dosage form.

26. A composition according to any of claims 20 to 24 wherein said composition contains per dosage form 10 to 300 mg of said calcium salt, with the total weight of the active ingredients being 10 to 300 mg per dosage form.

27. A composition according to claim 21 wherein said composition contains said calcium salt and the dimethyl fumarate in proportions of 10 to 290 parts by weight of said calcium salt and 290 to 10 parts by weight of dimethyl fumarate, with the total weight of the active ingredients being 20 to 300 mg per dosage form.

28. A composition according to claim 27 wherein said calcium salt is the calcium salt of fumaric acid monoethyl or monomethyl ester.

29. A composition according to claim 23 wherein said composition contains said calcium salt, said zinc salt, and the dimethyl fumarate, in proportions of 10 to 250 parts by weight of said calcium salt, 1 to 50 parts by weight of said zinc salt, and 1 to 50 parts by weight of dimethyl fumarate, with the total weight of the active ingredients being 20 to 300 mg per dosage form.

30. A composition according to claim 19 wherein said composition contains the calcium, magnesium, and zinc salts of said fumaric acid monoalkyl ester, and the dimethyl fumarate in proportions of 10 to 250 parts by weight of said calcium salt, 1 to 50 parts by weight of said magnesium salt, 1 to 50 parts by weight of said zinc salt, and 250 to 10 parts by weight of the dimethyl fumarate, with the total weight of the active ingredients being 30 to 300 mg per dosage form.

31. A composition according to claim 30 wherein said calcium salt is the calcium salt of fumaric acid monoethyl ester or the calcium salt of fumaric acid monomethyl ester.

32. A composition according to claim 30 wherein said calcium salt, said magnesium salt, and said zinc salt are, respectively, the calcium, the magnesium, and the zinc salts of fumaric acid monoethyl ester.

33. A composition according to any of claims 19, 20, 21, 22, 23, 24, 25, 27, 28, 29, 30, 31, or 32 wherein the micro-tablets or micro-pellets are provided with an enteric coating.

34. A composition according to any of claims 19, 20, 21, 22, 23, 24, 25, 27, 28, 29, 30, 31, or 32 wherein the micro-tablets or micro-pellets are filled into capsules or sachets.

35. A composition according to claim 26 wherein the micro-tablets or micro-pellets are provided with an enteric coating.

36. A composition according to claim 26 wherein the micro-tablets or micro-pellets are filled into capsules or sachets.

37. A method for treatment of psoriatic arthritis, neurodermatitis, psoriasis, or enteritis regionalis Crohn, which method comprises administering to the patient a pharmaceutical composition comprising micro-tablets or micro-pellets which comprise at least one salt of a fumaric acid monoalkyl ester of the formula

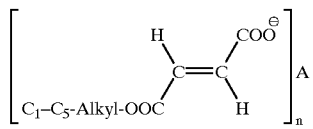

optionally in admixture with dialkyl fumarate of the formula

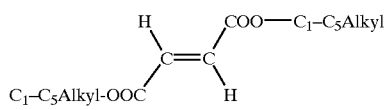

wherein A is a bivalent cation from the series consisting of Ca, Mg, Zn, or Fe, or a monovalent cation from the series Li, Na, or K, respectively, and n denotes the numeral 1 or 2 depending on the type of cation, and, optionally, at least one pharmaceutically acceptable excipient or vehicle.

38. A method according to claim 37 wherein said at least one salt of a fumaric acid monoalkyl ester is the calcium salt of fumaric acid monoethyl ester or of fumaric acid monomethyl ester.

39. A method according to claim 37 wherein said at least one salt of a fumaric acid monoalkyl ester is the calcium salt of said fumaric acid monoalkyl ester, and wherein dimethyl fumarate is in admixture with said calcium salt in said composition.

40. A method according to claim 38 wherein dimethylfumarate is in admixture with the calcium salt of fumaric acid monoethyl ester or fumaric acid monomethyl ester in said composition.

41. A method according to claim 37 wherein said at least one salt of a fumaric acid monoalkyl ester is a mixture of the calcium and the zinc salts of said fumaric acid monoalkyl ester, and wherein dimethylfumarate is in admixture with said calcium and zinc salts in said composition.

42. A method according to claim 37 wherein said at least one salt of a fumaric acid monoalkyl ester is a mixture of the calcium, the magnesium, and the zinc salts of fumaric acid monoethyl ester, and wherein dimethylfumarate is in admixture with said calcium, magnesium, and zinc salts in said composition.

43. A method according to claim 37 wherein said at least one salt of a fumaric acid monoalkyl ester is the calcium salt of said fumaric acid monoalkyl ester, and wherein said composition contains per dosage form 10 to 300 mg of said calcium salt, with the total weight of the active ingredients being 10 to 300 mg per dosage form.

44. A method according to any of claims 38 to 42 wherein said composition contains per dosage form 10 to 300 mg of said calcium salt, with the total weight of the active ingredients being 10 to 300 mg per dosage form.

45. A method according to claim 39 wherein said composition contains said calcium salt and the dimethyl fumarate in proportions of 10 to 290 parts by weight of said calcium salt and 290 to 10 parts by weight of dimethyl fumarate, with the total weight of the active ingredients being 20 to 300 mg per dosage form.

46. A method according to claim 45 wherein said calcium salt is the calcium salt of fumaric acid monoethyl or monomethyl ester.

47. A method according to claim 41 wherein said composition contains said calcium salt, said zinc salt, and the dimethyl fumarate, in proportions of 10 to 250 parts by weight of said calcium salt, 1 to 50 parts by weight of said zinc salt, and 1 to 50 parts by weight of dimethyl fumarate, with the total weight of the active ingredients being 20 to 300 mg per dosage form.

48. A method according to claim 37 wherein said composition contains the calcium, magnesium, and zinc salts of said fumaric acid monoalkyl ester, and the dimethyl fumarate in proportions of 10 to 250 parts by weight of said calcium salt, 1 to 50 parts by weight of said magnesium salt, 1 to 50 parts by weight of said zinc salt, and 250 to 10 parts by weight of the dimethyl fumarate, with the total weight of the active ingredients being 30 to 300 mg per dosage form.

49. A method according to claim 48 wherein said calcium salt is the calcium salt of fumaric acid monoethyl ester or the calcium salt of fumaric acid monomethyl ester.

50. A method according to claim 48 wherein said calcium salt, said magnesium salt, and said zinc salt are, respectively, the calcium, the magnesium, and the zinc salts of fumaric acid monoethyl ester.

51. A method according to any of claims 37, 38, 39, 40, 41, 42, 43, 45, 46, 47, 48, 49, or 50 wherein the micro-tablets or micro-pellets are provided with an enteric coating.

52. A method according to any of claims 37, 38, 39, 40, 41, 42, 43, 45, 46, 47, 48, 49, or 50 wherein the micro-tablets or micro-pellets are filled into capsules or sachets.

53. A method according to claim 44 wherein the micro-tablets or micro-pellets are provided with an enteric coating.

54. A method according to claim 44 wherein the micro-tablets or micro-pellets are filled into capsules or sachets.

* * * * *

UNITED STATES PATENT AND TRADEMARK OFFICE
CERTIFICATE OF CORRECTION

PATENT NO. : 6,355,676 B1
DATED : March 12, 2002
INVENTOR(S) : Joshi et al.

It is certified that error appears in the above-identified patent and that said Letters Patent is hereby corrected as shown below:

<u>Title page,</u>
Item [87], PCT Pub No.: reads "WO00/10681" and should read -- WO00/23068 --.
Item [87], PCT Pub. Date: reads "Mar. 2, 2000" and should read -- Apr. 27, 2000 --.

Signed and Sealed this

Twentieth Day of May, 2003

JAMES E. ROGAN
*Director of the United States Patent and Trademark Office*